(12) United States Patent
Leoni et al.

(10) Patent No.: US 6,342,481 B1
(45) Date of Patent: *Jan. 29, 2002

(54) OLIGOPEPTIDES DERIVED FROM C-REACTIVE PROTEIN FRAGMENTS

(75) Inventors: Flavio Leoni; Silvio Agozzino; Paolo Mascagni, all of Cinisello Balsamo (IT)

(73) Assignee: Italfarmaco S.p.A., Milan (IT)

( * ) Notice: Subject to any disclaimer, the term of this patent is extended or adjusted under 35 U.S.C. 154(b) by 0 days.

This patent is subject to a terminal disclaimer.

(21) Appl. No.: 09/439,164

(22) Filed: Nov. 12, 1999

Related U.S. Application Data

(63) Continuation-in-part of application No. 08/624,405, filed on Jun. 11, 1996, now Pat. No. 6,057,295.

(30) Foreign Application Priority Data

Dec. 10, 1993 (IT) .......................................... MI93A2154

(51) Int. Cl.[7] .............................................. A61K 38/00
(52) U.S. Cl. .......................... 514/18; 514/19; 530/330; 530/331
(58) Field of Search ...................... 514/18, 19; 530/330, 530/331

(56) References Cited

U.S. PATENT DOCUMENTS 4,353,823 A * 10/1982 Chipens et al. ....... 260/112.5 R
6,057,295 A * 5/2000 Caretto et al. ................ 514/18

FOREIGN PATENT DOCUMENTS

DE 2945239 A1 * 5/1981

OTHER PUBLICATIONS

CAPLUS DN 106:61216, Hahn, WO 8604334 A1, abstract only, 1993.*

CAPLUS DN 112:229807, Murphy et al., Pept. Res. (1988), 1(1), 36–41.*

CAPLUS DN 118:39381, Hocart et al., Innovation Perspect. Solid Phase Synth. Collect. Pap., Int. Symp., 1st (1990), Meeting Date 1989, 413–20.*

Robey et al., The Journal of Biological Chemistry, vol. 262, No. 15, (1987), pp. 7053–7057.*

Degrado, Advances in Protein Chemistry, vol. 39, 1988, pp. 51–124.*

* cited by examiner

*Primary Examiner*—Dwayne C. Jones
*Assistant Examiner*—C. Delacroix-Muirheid
(74) *Attorney, Agent, or Firm*—Walter H. Schneider

(57) ABSTRACT

The present invention relates to oligopeptide derived from fragments of the C-reactive protein (CRP), and to their use in the therapy of cardiovascular and inflammatory diseases.

6 Claims, No Drawings

SEQUENCE LISTING

```
<160> NUMBER OF SEQ ID NOS:  15

<210> SEQ ID NO 1
<211> LENGTH: 4
<212> TYPE: PRT
<213> ORGANISM: Artificial Sequence
<220> FEATURE:
<221> NAME/KEY: MOD_RES
<222> LOCATION: (1)
<223> OTHER INFORMATION: sarcosine
<223> OTHER INFORMATION: Description of Artificial Sequence:
      oligopeptides derived from fragments of the C-reactive protein

<400> SEQUENCE: 1

Xaa Lys Pro Arg
  1

<210> SEQ ID NO 2
<211> LENGTH: 3
<212> TYPE: PRT
<213> ORGANISM: Artificial Sequence
<220> FEATURE:
<221> NAME/KEY: MOD_RES
<222> LOCATION: (1)
<223> OTHER INFORMATION: H-(Et)Lys
<223> OTHER INFORMATION: Description of Artificial Sequence:
      oligopeptides derived from fragments of the C-reactive protein

<400> SEQUENCE: 2

Lys Pro Arg
  1

<210> SEQ ID NO 3
<211> LENGTH: 3
<212> TYPE: PRT
<213> ORGANISM: Artificial Sequence
<220> FEATURE:
<221> NAME/KEY: MOD_RES
```

```
<222> LOCATION: (1)
<223> OTHER INFORMATION: (Et)2Lys
<223> OTHER INFORMATION: Description of Artificial Sequence:
      oligopeptides derived from fragments of the C-reactive protein

<400> SEQUENCE: 3

Lys Pro Arg
  1

<210> SEQ ID NO 4
<211> LENGTH: 4
<212> TYPE: PRT
<213> ORGANISM: Artificial Sequence
<220> FEATURE:
<221> NAME/KEY: MOD_RES
<222> LOCATION: (2)
<223> OTHER INFORMATION: (Et)Lys
<223> OTHER INFORMATION: Description of Artificial Sequence:
      oligopeptides derived from fragments of the C-reactive protein

<400> SEQUENCE: 4

Gly Lys Pro Leu
  1

<210> SEQ ID NO 5
<211> LENGTH: 4
<212> TYPE: PRT
<213> ORGANISM: Artificial Sequence
<220> FEATURE:
<221> NAME/KEY: MOD_RES
<222> LOCATION: (2)
<223> OTHER INFORMATION: (Et)Lys
<221> NAME/KEY: MOD_RES
<222> LOCATION: (4)
<223> OTHER INFORMATION: agmantine
<223> OTHER INFORMATION: Description of Artificial Sequence:
      oligopeptides derived from fragments of the C-reactive protein

<400> SEQUENCE: 5

Gly Lys Pro Xaa
  1

<210> SEQ ID NO 6
<211> LENGTH: 3
<212> TYPE: PRT
<213> ORGANISM: Artificial Sequence
<220> FEATURE:
<221> NAME/KEY: MOD_RES
<222> LOCATION: (2)
<223> OTHER INFORMATION: (Et)Lys
<223> OTHER INFORMATION: Description of Artificial Sequence:
      oligopeptides derived from fragments of the C-reactive protein

<400> SEQUENCE: 6

Gly Lys Pro
  1

<210> SEQ ID NO 7
<211> LENGTH: 4
<212> TYPE: PRT
<213> ORGANISM: Artificial Sequence
<220> FEATURE:
<221> NAME/KEY: MOD_RES
<222> LOCATION: (2)
<223> OTHER INFORMATION: (Et)Lys
<223> OTHER INFORMATION: Description of Artificial Sequence:
      oligopeptides derived from fragments of the C-reactive protein

<400> SEQUENCE: 7

Leu Lys Pro Arg
```

```
<210> SEQ ID NO 8
<211> LENGTH: 4
<212> TYPE: PRT
<213> ORGANISM: Artificial Sequence
<220> FEATURE:
<221> NAME/KEY: MOD_RES
<222> LOCATION: (2)
<223> OTHER INFORMATION: (isoBu)Lys
<223> OTHER INFORMATION: Description of Artificial Sequence:
      oligopeptides derived from fragments of the C-reactive protein

<400> SEQUENCE: 8

Gly Lys Pro Arg
 1

<210> SEQ ID NO 9
<211> LENGTH: 3
<212> TYPE: PRT
<213> ORGANISM: Artificial Sequence
<220> FEATURE:
<221> NAME/KEY: MOD_RES
<222> LOCATION: (2)
<223> OTHER INFORMATION: (isoBut)Lys
<223> OTHER INFORMATION: Description of Artificial Sequence:
      oligopeptides derived from fragments of the C-reactive protein

<400> SEQUENCE: 9

Gly Lys Pro
 1

<210> SEQ ID NO 10
<211> LENGTH: 4
<212> TYPE: PRT
<213> ORGANISM: Artificial Sequence
<220> FEATURE:
<221> NAME/KEY: MOD_RES
<222> LOCATION: (2)
<223> OTHER INFORMATION: (Bzl)Lys
<223> OTHER INFORMATION: Description of Artificial Sequence:
      oligopeptides derived from fragments of the C-reactive protein

<400> SEQUENCE: 10

Gly Lys Pro Arg
 1

<210> SEQ ID NO 11
<211> LENGTH: 4
<212> TYPE: PRT
<213> ORGANISM: Artificial Sequence
<220> FEATURE:
<223> OTHER INFORMATION: Description of Artificial Sequence:
      oligopeptides derived from fragments of the C-reactive protein

<400> SEQUENCE: 11

Gly Pro Pro Arg
 1

<210> SEQ ID NO 12
<211> LENGTH: 2
<212> TYPE: PRT
<213> ORGANISM: Artificial Sequence
<220> FEATURE:
<221> NAME/KEY: MOD_RES
<222> LOCATION: (1)
<223> OTHER INFORMATION: (Et)Lys
<223> OTHER INFORMATION: Description of Artificial Sequence:
      oligopeptides derived from fragments of the C-reactive protein
```

```
<400> SEQUENCE: 12

Lys Pro
  1

<210> SEQ ID NO 13
<211> LENGTH: 4
<212> TYPE: PRT
<213> ORGANISM: Artificial Sequence
<220> FEATURE:
<221> NAME/KEY: MOD_RES
<222> LOCATION: (2)
<223> OTHER INFORMATION: (Et)Lys
<221> NAME/KEY: MOD_RES
<222> LOCATION: (4)
<223> OTHER INFORMATION: DArg
<223> OTHER INFORMATION: Description of Artificial Sequence:
      oligopeptides derived from fragments of the C-reactive protein

<400> SEQUENCE: 13

Gly Lys Pro Arg
  1

<210> SEQ ID NO 14
<211> LENGTH: 4
<212> TYPE: PRT
<213> ORGANISM: Artificial Sequence
<220> FEATURE:
<221> NAME/KEY: MOD_RES
<222> LOCATION: (2)
<223> OTHER INFORMATION: (Et)Lys
<223> OTHER INFORMATION: Description of Artificial Sequence:
      oligopeptides derived from fragments of the C-reactive protein

<400> SEQUENCE: 14

Gly Lys Pro Lys
  1

<210> SEQ ID NO 15
<211> LENGTH: 4
<212> TYPE: PRT
<213> ORGANISM: Artificial Sequence
<220> FEATURE:
<221> NAME/KEY: MOD_RES
<222> LOCATION: (2)
<223> OTHER INFORMATION: (Et)Lys
<223> OTHER INFORMATION: Description of Artificial Sequence:
      oligopeptides derived from fragments of the C-reactive protein

<400> SEQUENCE: 15

Gly Lys Pro Arg
```

OLIGOPEPTIDES DERIVED FROM C-REACTIVE PROTEIN FRAGMENTS

This application is a continuation-in-part of application Ser. No. 08/624,405 filed Jun. 11, 1996 now U.S. Pat. No. 6,057,295.

The present invention relates to oligopeptides derived from fragments of the C-reactive protein (hereinafter CRP), and to their use in the therapy of cardiovascular and inflammatory diseases.

CRP is a protein generally having a very low blood concentration, which rises up to two thousand times following inflammatory processes [J. J. Morley and I. Kushner, Am. N.Y. Acad. Sci., 389, 406–418 (1989)]. F. A. Robey et al., J. Biol. Chem., 262, No. 15, 7053–7057 (1987) disclose three CRP tetrapeptide sequences very similar to the ones of tuftsin. The chemically synthetized tetrapeptides stimulate the fagocytic leukocytes and the production of superoxide, and induce mononuclear cells to produce interleukin 1, in a tuftsin-like manner. Like tuftsin, the three CRP tetrapeptides are rapidly metabolized and inactivated by proteases in vivo.

It has been now surprisingly found that chemically modified analogues of said CRP tetrapeptide fragments are useful in the therapy of cardiovascular and inflammatory diseases, for example in the therapy of ischemia and/or ischemia and reperfusion state or the septic shock.

Therefore, the present invention relates to oligopeptides of formula (I)

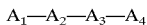

$$A_1-A_2-A_3-A_4 \quad (I)$$

wherein $A_1$ is an aminoacid residue selected from the group consisting of threonine, leucine, isoleucine, valine, sarcosine, alanine, glycine and $(C_{2-6})$acyl-glycine, or is absent;

$A_2$ is proline or N-α-substituted basic aminoacid residue selected from the group consisting of lysine, arginine and ornithine, N-α-substituted by at least one $(C_{1-6})$ alkyl, benzyl or $(C_{2-6})$acyl group;

$A_3$ is an aminoacid residue selected from the group consisting of proline, leucine, isoleucine and valine;

$A_4$ is an aminoacid residue selected from the group consisting of arginine, leucine and glutamine, optionally amidated or esterified at the C-terminal position, or is an agmatine residue, or is absent;

when $A_2$ is N-α-substituted lysine, both $A_1$ and $A_4$ may be absent; the side-chain groups of the above aminoacid residues and of the agmatine residue may be optionally substituted by one or more $(C_{1-6})$-alkyl, benzyl or $(C_{2-6})$acyl groups, and each of said aminoacid residues may be in D- or L-form, or in form of one of the possible diastereoisomers or enantiomers; and their salts with pharmaceutically acceptable acids or bases.

A preferred group of compounds according to the invention are the ones of formula (I) wherein $A_1$ is an aminoacid residue selected from the group consisting of glycine, threonine, leucine, isoleucine, valine, sarcosine, alanine $(C_{2-6})$acyl-glycine, or is absent;

$A_2$ is lysine, arginine or ornithine N-α-substituted by a $(C_{1-6})$alkyl, benzyl or $(C_{2-6})$acyl group; $A_3$ is proline; $A_4$ is glutamine, leucine, arginine, optionally amidated or esterified at the C-terminal position, or an agmatine residue, or is absent;

the side-chain groups of said aminoacid residue and of the agmatine residue may optionally be substituted by one or more substituents selected from the group consisting of $(C_{1-6})$alkyl, benzyl or $(C_{2-6})$acyl; and each of said aminoacid residue may be in D or L form, or in form of one of the possible diastereoisomers or enantiomers; and the pharmaceutically acceptable acid or base salts thereof.

As $(C_{1-6})$alkyl it is intended a group such as methyl, ethyl, propyl, i-propyl, butyl, sec-butyl, tert.-butyl, n-pentyl, 3-methyl-pentyl, n-hexyl group, and the relevant positional isomers. As $(C_{2-6})$acyl it is intended a group such as formyl, acetyl, propionyl, butyryl, pentanoyl, hexanoyl and the relevant positional isomers.

Another object of the present invention relates to the use of the oligopeptides of formula (I) as useful agents, in the therapy of cardiovascular and inflammatory diseases, such as those induced by ischemia and/or ischemia and reperfusion state and septic shock.

The compounds of the general formula (I) may be prepared employing peptide synthesis procedures, both in solid phase or in solution, known to the skilled in the art [see, for example, Merrifield, R. B., Biochemistry, 3, 1385 (1964)]. Unless otherwise mentioned, the aminoacid residues are intended to be used in L-configuration at the Cα.

Preferably, the synthesis is carried out in solution starting from the selected aminoacid and assembling the oligopeptide by a step-by-step addition of the desired aminoacids. Anyway, pre-constituted di- or tripeptide units may also be employed. Even if the synthesis of the oligopeptide may be started from any aminoacid, and may proceed both in the N-terminal or C-terminal direction, it is preferable to carry it out in the N-terminal direction. The aminoacids or, if desired, the pre-constituted di- or tripeptides may be used as such or in form of the relevant derivatives protected at the carboxy group by esterification, e.g. with tert.-butyl (tBu) group, or/and at the amine group by amidation, e.g. with benzyloxycarbonyl (Z), and, in case, suitably protected at the side-chain groups, e.g. with 2,2,5,7,8-pentametyl-chroman-6-sulfonyl (Pmc), tert.-butyloxycarbonyl (Boc) or trifluoroacetic acid (TFA). These protections may be effected by methods familiar to the skilled in the peptide chemistry.

Anyway, the above mentioned protected derivatives are commercially available products too. The protective group of the α-amino moiety is advantageously removed before the condensation with the subsequent aminoacid, for example through acidolysis with medium strong acids (e.g., trifluoroacetic acid), or through catalytic hydrogenolysis using gaseous hydrogen or hydrogen donors such as, for example, formic acid or salts thereof, triethylsylane, hydrazine in alkali, etc., selected in view of the aminoacid to deprotect and of the others, if present, in the presence of a suitable palladium catalyst. Then, the condensation with the subsequent aminoacid residue is carried out, such residue being suitably protected at the moieties not to be involved in said reaction.

Such condensation may be effected through one of the several known methods. Specifically, active esters may be used, e.g. succinimide (Su), fluoride (F), or condensing agents such as benzotriazol-1-yl-oxy-tris-(dimethylamino)-phosphonium hexafluorophosphate (BOP), bromo-tris-pirrolidium-phosphonium hexafluorophosphate (PyBroP), dicyclohexylcarbodiimide (DCC), etc., optionally in the presence of a catalyst such as 1-hydroxy-benzotriazole (HOBT), 4-dimethyl-amino-pyridine (DMAP), triethylamine (TEA), N-methyl-morpholine, N-methyl-imidazole etc.

As for the N α-alkyl-derivatives of aminoacids, they are obtained by treatment with a suitable aldehyde, at low temperature, in the presence of cianoborohydride, selective reducing agent, in a polar solvent, preferably methanol.

When an oligopeptide of formula (I) having the C-terminal position in form of an amide is desired, commercially available aminoacids bearing such moiety may be employed as starting materials, or the C-terminal aminoacid may be amidated with an HOBT ammonium salt or, when $A_4$ is an agmatine residue, with agmatine itself.

The compounds of formula (I) wherein $A_1$ and/or $A_2$ are acylated aminoacid residues, are obtained by treatment with a suitable acyl-anhydride, at low temperature, in the presence of a catalyst such as DMAP. Alternatively, commercially available N α-acyl-aminoacid residues may be employed.

The resulting products may be purified by crystallization from suitable solvents or, if necessary, by known chromatographic techniques such as reversed-phase chromatography and ion-exchange chromatography.

Hereinbelow, examples of preparation of some modified oligopeptides according to the invention are provided.

HPLC analysis of the aminoacid derivatives, of the protected fragments and of the modified oligopeptides were carried out at the following experimental conditions:

Column: Lichrosorb RP-18;
Temperature: 25° C. (unless otherwise mentioned)
Flow: 1.5 ml/min
Detector: Jasco 875-UV (230nm)
Eluent A: 90% water, 10% acetonitrile, 0.1% trifluoroacetic acid. (TFA)
Eluent B: acetonitrile, 0.1% TFA
Eluent C: water, 0.1% TFA
Gradients: (I): from 0 to 40% B in A (20'), to 80% B in A (10')
(II): from 0 to 50% A in C (20'), to 100% A (3'), to 40% B in A 20'.

Unless otherwise mentioned, all the synthetic steps are carried out at room temperature.

The composition and the ratio of aminoacids were determined after hydrolysis with HCl 6M at 110° C. for 22 hours, by a Beckman SYSTEM GOLD aminoacid analyzer.

To be more clear, the meanings of the abbreviations employed in the following examples are listed hereinbelow:

BDHA-Cl=benzyldimethylhexadecylammonium chloride
Boc=tert.-butyloxycarbonyl
(Boc)2O=di-tert.butyl-dicarbonate
BOP=benzotriazol-1-yl-oxy-tris-(dimethylammino)-phosphonium hexafluorophosphate
BSA=N,O-bis(trimethylsilyl)-acetamide
DCC=dicyclohexylcarbodiimide
DMAP=4-dimethylamino-pyridina
DMF=dimethylformamide
F=fluoride
HOBT=1-hydroxy-benzotriazole
Pmc=2,2,5,7,8-pentamethyl-chroman-6-sulfonyl
PyBrop=bromo-tris-pirrolidinium-phosphonium hexafluorophosphate
tBu=tert.-butyl
TBAF=tetrabutylammonium fluoride
TEA=triethylamine
TFA=trifluoroacetic acid
Su=succinimide
Z=benzyloxycarbonyl

EXAMPLE 1

H-Sar-Lys-Pro-Arg-OH.2AcOH

A] A slurry of 6.9 g (12 mmoles) of Z-Arg(Pmc)-OH in 60 ml of dichloroethane was added with 8.64 ml (36 mmoles) of N,N-dimethylformamide-di-tert.-butyl-acetale, in 60 minutes at 50° C. At the end of the addition, the reaction mixture was kept under stirring for 40 minutes at 50° C., then it was added with 20 ml of an aqueous solution of 5% sodium hydrocarbonate. The dichloroethane was evaporated under vacuum and the aqueous phase was diluted with 100 ml of ethyl acetate. The organic phase was separated and washed with an aqueous solution of 5% sodium hydrocarbonate and with a saturated aqueous solution of sodium chloride. The organic phase was then anhydrified and evaporated under vacuum, and the resulting crude was purified on a silica gel column (eluent: ethyl acetate/n-hexane 6:4). There were obtained 3.4 g of Z-Arg(Pmc)-OtBu (HPLC, gradient (I): R.t. 32 min.; purity 99%).

B] A solution of 3.385 g (5.36 mmoles) of the compound under A] in 80 ml of methanol was added with 1.416 g (21.44 mmoles) of ammonium formate in 3 ml of water, and Pd sponge (about 1 g). The reaction mixture was slowly stirred for about 2 hours at room temperature. After filtering the catalyst off, the solvent was evaporated under vacuum, and the residue taken up in ethyl acetate and washed with an aqueous solution of 5% sodium hydrocarbonate, then with water till neutrality. The organic phase was anhydrified and evaporated under vacuum yielding 2.88 g of H-Arg(Pmc)-OtBu.HCOOH (HPLC, gradient (I): R.t. 23.40 min.; purity 99.3%).

C] The compound under B] was dissolved in 30 ml of DMF/methylene chloride 1:1. Separately, 1.403 g (5.63 mmoles) of Z-Pro-OH were dissolved in 20 ml of DMF/methylene chloride 1:1, added with BOP (2.49 g, 5.63 mmoles), HOBT (0.76 g, 5.63 mmoles) and TEA (1.56 ml, 11:26 mmoles). The two solutions were admixed and the resulting reaction mixture was stirred for 1 hour. The solvent was then evaporated under vacuum and the residue taken up in ethyl acetate and washed with 5% sodium hydrocarbonate and water. The organic phase was anhydrified and evaporated under vacuum, and the residue was triturated in ethyl ether, thus yielding 3.71 g of Z-Pro-Arg(Pmc)-OtBu (HPLC, gradient (I): R.t. 29.49 min.; purity 99.6%).

D] A solution of 3.709 g (5.08 mmoles) of the compound under C], in 50 ml of methanol, was added with 350 mg of Pd/C under nitrogen, and sequentially, very slowly, with 4 ml (24 mmoles) of triethylsylane. After about 2 hours, the reaction mixture was filtered and the solvent evaporated under vacuum thus yielding 3.01 g of H-Pro-Arg(Pmc)-OtBu (HPLC, gradient (I): R.t. 24.25 min.; purity 99.56%):

E] The compound under D] (2.375 g, 4 mmoles) was dissolved in 20 ml of DMF/methylene chloride 1:1 v/v. Z-Lys(Boc)-OH (1.826 g, 4.8 mmoles) was dissolved in 20 ml of the same mixture, then added with BOP (2.12 g, 4.8 mmoles), HOBT (0.648 g, 4.8 mmoles) and TEA (1.33 ml, 9.6 mmoles). The two solutions were admixed and such reaction mixture was left under stirring for 1 hour, then was treated as described under C]. The residue was triturated in ethyl ether, thus yielding 3.64 g of Z-Lys(Boc)-Pro-Arg(Pmc)-OtBu.

F] A solution of 3.64 g (3.8 mmoles) of the compound under E], in 70 ml of methanol, was added with 1.321 g (20 mmoles) of ammonium formate in 3 ml of water, and about 1 g of fresh Pd sponge. The procedure described under B] was then applied yielding 3.27 g of H-Lys(Boc)-Pro-Arg(Pmc)-OtBu.

G] Z-Sar-OH (0.196 g, 0.88 mmole) was dissolved in 4 ml of DMF/methylene chloride 1:1 v/v, and sequentially added with BOP (0.39 g, 0.88 mmole), HOBT (0.119 g, 0.88 mmole), TEA (0.24 ml, 1.76 mmoles) and the compound under F] (0.694 g, 0.8 mmole) dissolved in 4 ml of the same mixture. The solution was left under stirring for 1 hour. The solvent was then evaporated under vacuum and the residue taken up in ethyl acetate and washed with 5% sodium hydrocarbonate, 2.5% potassium hydrogen sulfate and water till neutrality. The organic phase was anhydrified and evaporated under vacuum and the residue triturated in ethyl ether yielding 0.746 g of Z-Sar-Lys(Boc)-Pro-Arg(Pmc)-OtBu.

H] The compound under G] (0.746 g, 0.726 mmole) was dissolved in 10 ml of 95% TFA in water. After 75 minutes the reaction mixture was diluted with water and evaporated under vacuum. The residue was taken up in water, washed with ethyl ether and freeze-dried. The resulting product was purified by reversed-phase displacement chromatography. The product was dissolved in 3 ml of an aqueous solution of TFA (0.1% v/v) and charged at a flow of 0.5 ml/min on a VYDAC C18 column (250×10 mm) previously equilibrated with water containing TFA (0.1% v/v). The column was then eluted with a 50 mM aqueous solution of BDHA-Cl containing TFA (0.1% v/v), at 0.5 ml/min. After about 1 hour of elution, 0.5 ml-fractions were collected until the displacer elution. The fractions were analyzed by HPLC and the ones containing the pure product were joined and freeze-dried. There was obtained 0.2 g of Z-Sar-Lys-Pro-Arg-OH (HPLC, gradient (I): R.t. 11.04 min.; purity >95%).

I] The compound under H] (0.2 g, 0.28 mmole) was dissolved in 85% formic acid (5 ml) and added with fresh Pd sponge. The reaction mixture was left under mild stirring for 100 minutes. After filtering the catalyst off, the reaction mixture was diluted with water and freeze-dried. The product was purified by ion-exchange chromatography on an S-Sepharose F/F column (16×200 mm), eluting with a gradient of ammonium acetate at pH 5 from 0.015 M to 0.15 M in 300 minutes, at 3 ml/min. The collected fractions were analyzed by HPLC and the ones containing the pure product were joined and freeze-dried more times yielding 0.1 g of the title product.

HPLC: gradient (II) R.t. 7.30 min., purity >99%. FAB-MS: m/z=471 amu [M+H]+. $^1$H-NMR (200 MHz; DMSO): d (1H; NH-Lys) 8.06; d (1H; NH-Arg) 7.17; m (1H; Cα-Pro) 4.63; m (1H; Cα-Lys) 4.32÷4.24; q (1H; Cα-Arg) 3.79; m (1H; Cδ-Pro) 3.70; s (2H; Cα-Sar) 3.05; t (3H; Cα-Arg) 3.03; t (2H; Cε-Lys) 2.75; s (3H; CH$_3$-Sar) 2.24; m (4H; Cβ+γ-Pro) 1.99÷1.85; s (6H; CH$_3$COO$^-$) 1.81; m (10H; Cβ+γ-Arg; Cβ+γ+δ-Lys) 1.72÷1.29.

EXAMPLE 2

H-(Et)Lys-Pro-Arg-OH.2AcOH

A] The compound of Example 1, F] (0.96 g, 1.1 mmoles) was dissolved in 8 ml of methanol and added with 0.071 g (1.12 mmoles) of sodium cyanoborohydride. The reaction mixture was cooled to −15° C. and added with 0.062 ml (1.12 mmoles) of acetaldehyde. After 60 minutes the reaction mixture was evaporated under vacuum and the residue was taken up in water and added with HCl till pH 3. The precipitate was filtered and washed with HCl pH=3. There was obtained 0.825 g of a white solid formed at 70% by H-(Et)Lys(Boc)-Pro-Arg(Pmc)-OtBu and at 26% by the dialkylation by-product.

B] 0.4 g of the compound under A] was purified by silica gel chromatography on a Lobar LiChroprep Si 60 column, 40–63 μm (31×2.5 cm) previously equilibrated with chloroform/methanol (9/1 v/v). The column was then eluted with the same mixture at a flow of 8 ml/min. The fractions containing the pure product were joined and the solvent was evaporated under vacuum. There was obtained 0.28 g of H-(Et)Lys(Boc)-Pro-Arg(Pmc)-OtBu.

HPLC: gradient (I) R.t. 28.5 min.; purity >99%.

C] The compound under B] (0.28 g, 0.33 mmole) was dissolved in 6 ml of 95% TFA in water. After 70 minutes, the reaction mixture was diluted with water and evaporated under vacuum. The residue was taken up in water, washed with ethyl ether and freeze-dried. The product was purified by ion-exchange chromatography with a CM-Sephadex C-25 column (16×200 mm) by eluting at 3 ml/min with a gradient of ammonium acetate at pH=6 from 0.02M to 0.2M in 270 minutes. The collected fractions were analyzed by HPLC, and the ones containing the pure product were pooled and freeze-dried more times, yielding 0.14 g of the title product.

HPLC: (column temperature: 60° C.) gradient (II) R.t. 7.15 min; purity >99%. FAB-MS: m/z=428 amu [M+H]+. $^1$H-NMR (200 MHz; DMSO): d (1H; NH-Arg) 7.15; m (1H; Cα-Pro) 4.30; q (1H; Cα-Arg) 3.79; m (2H; Cδ-Pro) 3.64; m (1H; Cα-Lys) 3.41; m (2H; Cδ-Arg) 3.02; m (2H; Cε-Lys) 2.75; q (2H; CH$_2$-Et) 2.44; m (14H; Cβ- and CγPro, Lys and -Arg, Cδ-Lys) 2.11÷1.21; s (6H; CH$_3$COO$^-$) 1.80; t (3H; CH$_3$-Et) 0.97.

EXAMPLE 3

(Et)2Lys-Pro-Arg-OH.2AcOH

A] 0.425 g of the compound of Example 2, A] was dissolved in 7 ml of methanol and added with 0.063 g (1 mmole) of sodium cianoborohydride. The reaction mixture was cooled to −15° C. and added with 0.155 ml (2.5 mmoles) of acetaldehyde. After 90 minutes the reaction mixture was evaporated under vacuum and the residue slurried in water and added with HCl to pH=3. The resulting precipitate was filtered and washed with hydrochloric acid at pH=3. There were obtained 0.4 g of (Et)2Lys(Boc)-Pro-Arg(Pmc)-OtBu.

HPLC: gradient (I) R.t. 30.3 min.; purity >98%.

B] The compound under A] (0.4 g, 0.455 mmole) was treated as in Example 2, C]. There was obtained 0.14 g of the title product.

HPLC: (column temperature: 60° C) gradient (II) R.t. 11.08 min.; purity >99%.

FAB-MS: m/z=456 amu [M+H]+. $^1$H-NMR (200 MHz, DMSO): d (1H; NH-Arg) 7.08; m (1H; Cα-Pro) 4.21; m (3H; Cα-Arg and Cδ-Pro) 3.98÷3.65; m (1H; Cα-Lys) 3.54; m (2H; Cδ-Arg) 3.03; m (2H; Cε-Lys) 2.75; (2H; CH$_2$-Et) 2.38; m (2H; CH$_2$-Et) 2.36; m (4H; Cβ- and Cγ-Pro) 2.18÷1.81; s (6H; CH$_3$COO$^-$) 1.76; m (10H; Cβ- and Cγ-Lys and -Arg and Cδ-Lys) 1.74÷1.33; t (6H; CH$_3$-Et) 0.96.

EXAMPLE 4

H-Gly-(Et)Lys-Pro-Leu-OH.AcOH

A] Z-Lys(Boc)-OH (1.487 g, 3.8 mmoles) was dissolved in 15 ml of DMF/methylene chloride (1:1 v/v) and sequentially added with BOP (1.72 g, 3.8 mmoles), HOBT (0.52 g, 3.8 mmoles), TEA (1.08 ml, 7.8 mmoles) and H-Pro-OtBu (0.623 g, 3 mmoles) dissolved in 15 ml of the same mixture. The solution was left under stirring for 1 hour. The solvent was then evaporated under vacuum, and the residue taken up in ethyl acetate and washed with 5% sodium hydrocarbonate in water, 2.5% potassium hydrogen sulfate in water, and water to neutrality. The organic phase was anhydrified and evaporated under vacuum, and the residue triturated in ethyl ether yielding 1.6 g of Z-Lys(Boc)-Pro-OtBu.

B] The compound under A] (5.33 g, 10 mmoles) was dissolved in 130 ml of absolute ethanol, in the presence of Pd/C. Acetaldehyde (0.745 ml, 12 mmoles) was then added dropwise in 30 minutes, dissolved in 20 ml of absolute ethanol, followed by triethylsilane (9.56 ml, 60 mmoles) in 60 minutes. After 75 minutes the catalyst was filtered off and the solvent evaporated under vacuum. The oily residue was dissolved in 50 ml of anhydrous ethyl ether and added with 3 ml of ethyl acetate saturated with HCl. The resulting precipitate was filtered and dried under vacuum. There were obtained 4.25 g of H-(Et)Lys(Boc)-Pro-OtBu.HCl.

HPLC: gradient (I) R.t. 19.83 min; purity >98%.

C] Z-Gly-OH (3.78 g, 18 mmoles) was dissolved in a mixture of 12 ml of DMF and 67 ml of methylene chloride. The solution was cooled to −15° C. and added with DCC (1.86 g, 9.03 mmoles). After 15 minutes the reaction mixture was filtered and added to the compound under B] (2.8 g, 6.02 mmoles) dissolved in 40 ml of methylene chloride. After the addition of N-methyl-morpholine (0.66 ml, 6.02 mmoles) the reaction mixture was kept at 35° C. for 60 minutes. The solvent was evaporated under vacuum and the residue taken up in ethyl acetate and washed with 5% sodium hydrocarbonate in water and 2.5% potassium hydrogen sulfate in water. The organic phase was anhydrified and evaporated under vacuum. There were obtained 3.7 g of Z-Gly-(Et)Lys(Boc)-Pro-OtBu.

HPLC: gradient (I) R.t. 28.60 min; purity: 94%.

D] The compound under C] (3.7 g, 6 mmoles) was dissolved in 15 ml of 95% TFA in water. After 15 minutes the reaction mixture was slowly poured into ethyl ether and the resulting precipitate was filtered and dried under vacuum. There were obtained 2.9 g of Z-Gly-(Et)Lys-Pro-OH.

HPLC: gradient (I) R.t. 14.93 min; purity: 94%.

E] The compound under D] (1 g, 1.73 mmoles) was dissolved in 6.92 ml of dioxane/sodium hydroxide 0.5M in water (1/1 v/v). The solution was cooled to 0° C. and added with (Boc)2O (0.415 g, 1.903 mmoles). The reaction mixture was kept at room temperature for 45 minutes at pH=12. The solvent was evaporated under vacuum and the residue taken up in water and washed with ethyl ether. The aqueous phase was acidified to pH=3 and extracted in 30 ml of ethyl acetate. The organic phase was anhydrified and evaporated under vacuum. There was obtained 0.96 g of Z-Gly-(Et)Lys(Boc)-Pro-OH.

HPLC: gradient (I) R.t. 23.04 min; purity 92%.

F] The compound under E] (0.281 g, 0.5 mmole) was dissolved in 4 ml of DMF/methylene chloride 1:1, and added with BOP (0.221 g, 0.5 mmole), HOBT (0.067 g, 0.5 mmole), TEA (0.219 ml, 1.57 mmoles) and H-Leu-OtBu.HCl (0.117 g, 0.525 mmole). The procedure of Example 1, C] was then applied. There was obtained 0.365 g of Z-Gly-(Et)Lys(Boc)-Pro-Leu-OtBu.

HPLC: gradient (1) R.t. 29.86 min; purity >99%.

G] Starting from the compound under F] (0.365 g, 0.5 mmole), and substantially proceeding as described in Example 1, H-I], there was obtained 0.155 g of the title product.

HPLC: gradient (I) R.t. 6.3 min; purity 98%. FAB-MS: m/z=442 amu [M+H]+. $^1$H-NMR (200 MHz; DMSO): d (1H; NH-Leu) 6.93; m (1H; Cα-Lys) 5.23; m (1H; Cα-Pro) 4.15; m (1H; Cα-Leu) 3.84; m (6H; Cα-Gly, Cδ-Pro and CH$_2$-Et) 3.72÷3.03; m (2H; Cε-Lys) 2.75; m (4H; Cβ- and Cγ-Pro) 2.17÷1.77; s (3H; CH$_3$COO$^-$) 1.85; m (9H; Cβ- and Cγ-Lys and -Leu, Cδ-Lys) 1.68÷1.05; t (3H; CH$_3$-Et) 0.96; d (3H; CH$_3$-Leu) 0.88; d (3H; CH$_3$-Leu) 0.86.

EXAMPLE 5

H-Gly-(Et)Lys-Pro-Agm.3AcOH

A] The compound of Example 4, E], (0.425 g, 0.75 mmole), was dissolved in 5 ml of ethyl acetate N-hydroxysuccinimide (0.103 g, 0.9 mmole), DCC (0.186 g, 0.9 mmole), and sequentially added with sodium carbonate (0.095 g, 0.9 mmole), agmatine sulfate (0.411 g, 1.8 mmoles) and N-methyl-imidazole (0.072 ml, 0.9 mmole). The reaction mixture was kept under stirring for 30 minutes at room temperature, then the mixture was brought to pH 3 and washed with ethyl acetate. The aqueous phase was freeze-dried. There was obtained 0.5 g of Z-Gly(Et)Lys(Boc)-Pro-Agm.

HPLC: gradient (I) R.t. 20.6 min; purity 85%.

B] Starting from the compound under A] (0.5 g, 0.74 mmole) and proceeding as described in Example 1, H–I], there was obtained 0.169 g of the title product.

HPLC: column temperature: 60° C.; gradient (II) R.t. 13.87 min; purity >99%. FAB-MS: m/z=441 amu [M+H]+. $^1$H-NMR (200 MHz; DMSO): t (1H; NH-Agm) 7.98; m (1H; Cα-Lys) 5.26; m (1H; Cα-Pro) 4.15; m (10H; Cα-Gly, Cα-Agm, Cδ-Pro, Cδ-Agm and CH$_2$-Et) 3.65÷2.91; m (2H; Cε-Lys) 2.66; m (14H; Cβ- and Cγ-Lys, -Pro and -Agm, and Cδ-Lys) 2.18÷1.16; s (9H; CH$_3$COO$^-$) 1.76; t (3H; CH$_3$-Et) 0.99.

EXAMPLE 6

H-Gly-(Et)Lys-Pro-OH.2AcOH

Starting from the compound of Example 4, D] (0.2 g, 0.347 mmole) and proceeding as described in Example 1, I], there was obtained 0.085 g of the title product.

HPLC: (column temperature: 60° C); gradient (II) R.t. 9.32 min; purity >99%. FAB-MS: m/z=329 amu [M+H]+. $^1$H-NMR (200 MHz; DMSO): m (1H; Cα-Lys) 5.16; m (1H; Cα-Pro) 4.05; m (6H; Cα-Gly and Cδ-Pro and CH$_2$-Et) 3.87÷2.92; m (2H; Cε-Lys) 2.67; m (4H; Cβ- and Cγ-Pro) 2.10÷1.65; s (6H; CH$_3$COO$^-$) 1.78; m (6H; Cβ+γ+δ-Lys) 1.59÷1.24; t (1.3H; CH$_3$-Et) 1.06; t (1.7H; CH$_3$-Et) 1.02.

EXAMPLE 7

H-Leu-(Et)Lys-Pro-Arg-OH.2AcOH

A] The compound of Example 4, B] (0.732 g, 1.5 mmoles) was dissolved, under nitrogen, in 8 ml of acetonitrile. There was then added 0.733 ml (3 mmoles) of BSA, 1.6 g (6 mmoles) of Z-Leu-F (L. A. Carpino, E. M. E. Mansour, D. Sadat-Aalaee, J. Org. Chem., 1991, 56, 2611–2614) and 0.094 g (0.3 mmole) of TBAF dissolved in 2 ml of acetonitrile. The reaction mixture was kept under stirring for 240 minutes at room temperature. The solvent was then evaporated under vacuum and the residue taken up in ethyl acetate and washed with 5% sodium hydrocarbonate and 2.5% potassium hydrogen sulfate to neutrality. The organic phase was anhydrified and evaporated under vacuum and the residue was purified by silica gel chromatography using a Lobar LiChroprep Si 60 column, 40–63 mm, (44×3.7 cm) previously equilibrated in hexane/ethyl acetate (7/3 v/v). The column was eluted with the same mixture at 16 ml/min. The fractions containing the pure product were collected and the solvent evaporated under vacuum. There was obtained 0.5 g of Z-Leu-(Et)Lys(Boc)-Pro-OtBu.

HPLC: gradient (I) R.t. 31.5 min; purity 94%.

B] The compound under A] (0.5 g, 0.74 mmole) was treated as described in Example 4, D–E]. There was obtained 0.43 g of Z-Leu-(Et)Lys(Boc)-Pro-OH.

HPLC: gradient (I) R.t. 31.5 min; purity >98%.

C] The compound under B] (0.43 g, 0.695 mmole) was dissolved in 9 ml of 1,2-dimethoxyethane and added with N-hydroxysuccinimide (0.128 g, 1.112 mmoles) and, after cooling to −20° C., DCC (0.215 g, 1.042 mmoles). After 15 minutes the reaction mixture was filtered and the resulting solution was added with H-Arg-OH dissolved in 21 ml of DMF/KCl 0.15M in water (2/1 v/v). The reaction mixture was kept under stirring for 110 minutes at room temperature. The solvent was then evaporated under vacuum and the residue taken up several times in absolute ethanol, and filtered. There was obtained 0.455 g of Z-Leu-(Et)Lys(Boc)-Pro-Arg-OH.

HPLC: gradient (I) R.t. 24.38 min; purity 84%.

D] The compound under C] was treated as described in Example 1, H], thus yielding Z-Leu-(Et)Lys-Pro-Arg-OH.TFA (ITF 1929).

HPLC: gradient (I) R.t. 17.63 min; purity 98%. FAB-MS: m/z=676 amu [M+H]+. $^1$H-NMR (200 MHz; DMSO): t (1H; NHε-Arg) 7.77; d (1H; NH-Leu) 7.68; m (5H; CH-aryl) 7.37; d (1H; NHα-Arg) 7.34; m (1H; Cα-Lys) 5.15; s (2H; CH$_2$-Z) 5.03; m (1H; Cα-Leu) 4.42; m (1H; Cα-Pro) 4.26; m (1H; Cα-Arg) 3.99; m (4H; Cδ-Pro and CH$_2$-Et) 3.68÷3.18; m (2H; Cδ-Arg) 3.11; m (2H; CHε-Lys) 2.74; m (17H; Cβ and Cγ-Leu, -Lys, -Pro and -Arg, and Cδ-Lys) 2.18÷1.19; t (3H; CH$_3$-Et) 1.12; d (6H; CH$_3$-Leu) 0.89.

E] The compound under D] (0.341 g, 0.44 mmole) was treated as described in Example 1, I]. There was obtained 0.06 g of the title product.

HPLC: gradient (II) R.t. 29.13 min; purity 97% FAB-MS: m/z=541 amu [M+H]+. $^1$H-NMR (200 MHz; DMSO): d (1H; NH-Arg) 7.10; m (1H; Cα-Lys) 5.20; m (1H; Cα-Pro) 4.19; m (1H; Cα-Arg) 3.81; m (5H; Cα-Lys, CH$_2$-Et and Cδ-Pro) 3.66÷3.10; m (2H; Cδ-Arg) 3.03; m (2H; Cε-Lys) 2.74; m (17H; Cβ and Cγ-Leu, -Lys, -Pro and -Arg, and Cδ-Lys) 2.10÷1.18; s (6H; CH$_3$COO$^-$) 1.77; t (3H; CH$_3$-Et) 1.03; d (3H; CH$_3$-Leu) 0.89; d (3H; CH$_3$-Leu) 0.87.

EXAMPLE 8

H-Gly-(isoBu)Lys-Pro-Arg-OH.2AcOH

A] The compound under 4, A] (1.59 g, 2.9 mmoles) was dissolved in 20 ml of methanol, and the resulting solution was added with ammonium formate (0.731 g, 11.6 mmoles) dissolved in 0.6 ml of water, and fresh Pd sponge (about 0.5 g). After 2 hours the catalyst was filtered off and the solvent was evaporated under vacuum. The residue was taken up in 50 ml of ethyl acetate and washed with 5% sodium hydrocarbonate in water and water to neutrality. The organic phase was anhydrified and evaporated under vacuum to yield 1.119 g of H-Lys(Boc)-Pro-OtBu.HCOOH.

B] The compound under A] (2.38 g, 5.95 mmoles) was dissolved in 34 ml of methanol and added with 20.4 ml of acetic acid. The reaction mixture was cooled to −20° C. and, after dropwise addition isobutyraldehyde (1.36 ml, 14.87 mmoles), added with sodium cianoborohydride (0.748 g, 11.9 mmoles). The reaction mixture was kept under stirring for 100 minutes at room temperature. The solvent was then evaporated under vacuum and the residue was taken up in ethyl acetate and washed with 5% sodium carbonate, HCl at pH=2.5 and water till neutrality. The organic phase was anhydrified and evaporated under vacuum. There were obtained 2.65 g of H-(isoBu)Lys(Boc)-Pro-OtBu.

HPLC: gradient (I) R.t. 22.85 min; purity 97%.

C] Starting from the compound under B] (2.2 g, 4.8 mmoles) and Z-Gly-F (4.2 g, 20 mmoles) and substantially operating as described in Example 7, A–D], there was obtained 0.2 g of the title product.

HPLC: gradient (II) R.t. 12.58 min; purity >98%. FAB-MS: m/z=513 amu [M+H]+. $^1$H-NMR (200 MHz; DMSO): d (1H; NH-Arg) 7.09; m (1H; Cα-Lys) 5.25; m (0.3H; Cα-Pro) 4.43; m (0.7H; Cα-Pro) 4.16; m (3H; Cα-Arg and Cδ-Pro) 3.83÷3.56; m (2H; Cα-Gly) 3.38; m (4H; CH$_2$-iBu and Cα-Arg) 3.09÷2.93; m (2H; Cε-Lys) 2.75; m (15H; Cβ- and Cγ-Lys, -Pro and -Arg, Cδ-Lys and CH-iBu) 2.13÷1.16; s (6H; CH$_3$COO$^-$) 1.79; d (2.1H; CH$_3$-iBu) 0.81; d (3H; CH$_3$-iBu) 0.76; d (0.9H; CH$_3$-iBu) 0.69.

EXAMPLE 9

H-Gly-(isoBut)Lys-Pro-OH.AcOH

Starting from the compound obtained in Example 8, B] (0.455 g, 1 mmole) and Z-Gly fluoride (0.84 g, 4 mmoles), and substantially operating as described in Example 8, B] and then 2, C], there was obtained 0.172 g of the title product.

HPLC: (column temperature: 60° C.), gradient (II) R.t. 23.48 min; purity >98%. FAB-MS: m/z=357 amu [M+H]+. $^1$H-NMR (200 MHz; DMSO): m (1H; Cα-Lys) 5.13; m (0.3H; Cα-Pro) 4.30; m (0.7H; Cα-Pro) 4.00; m (4H; Cα-Gly and Cδ-Pro) 3.68÷3.31; m (2H; CH$_2$-iBu) 3.03; m (2H; Cε-Lys) 2.81÷2.61; m (11H; Cβ and Cγ-Lys and -Pro, Cδ-Lys and CH-iBu) 2.05÷1.24; s (3H; CH$_3$COO$^-$) 1.86; d (2.1H; CH$_3$-iBu) 0.82; d (3H; CH$_3$-iBu) 0.77; d (0.9H; CH$_3$-iBu) 0.69.

EXAMPLE 10

H-Gly-(Bzl)Lys-Pro-Arg-OH.2AcOH

Starting from the compound of Example 8, A] (1.36 g, 3 mmoles) and benzaldehyde (0.546 ml, 5.4 mmoles), and substantially following the procedure of Example 8, B–C], there was obtained 0.395 g of the title product.

HPLC: gradient (II) R.t. 27.85 min; purity >99%. FAB-MS: m/z=546 amu [M+H]+. $^1$H-NMR (200 MHz; DMSO): m (6H; CH-aryl and NH-Arg) 7.39÷6.97; m (0.7H; Cα-Lys) 5.42; m (0.3H; Cα-Lys) 4.93; m (2H; Cα-Pro and Cα-Arg) 4.65÷4.42; m (4H; Cα-Gly and Cδ-Pro) 4.00÷3.43; m (2H; CH$_2$-aryl) 3.30; m (2H; Cδ-Arg) 3.03; m (2H; Cε-Lys) 2.75; m (14H; Cβ- and Cγ-Lys, -Pro and -Arg, and Cδ-Lys) 2.29÷1.14; s (6H; CH$_3$COO$^-$) 1.79.

EXAMPLE 11

H-Gly-Pro-Pro-Arg-OH.AcOH

A] Starting from H-Pro-OtBu.HCl (0.315 g, 1.5 mmoles) and Z-Pro-OH (0.397 g, 1.59 mmoles) the procedure of Example 1, C–D] was substantially applied. There was obtained 0.4 g of H-Pro-Pro-OtBu.

HPLC: gradient (I) R.t. 11.38 min; purity 93%.

B] Starting from Z-Gly-OH (0.333 g, 1.59 mmoles) and the compound under A] (0.4 g, 1.5 mmoles), the procedure of Example 1, G–H] was substantially applied, thus obtaining 0.6 g of Z-Gly-Pro-Pro-OH.

HPLC: gradient (I) R.t. 14.81 min; purity >98%.

C] The compound under B] was treated substantially as described in Example 7, C–D]. There was obtained 0.045 g of the title product.

HPLC: (column temperature: 60° C.) gradient (II) R.t. 12.06 min; purity >98%. FAB-MS: m/z=426 amu [M+H]+. $^1$H-NMR (200 MHz; DMSO): d (1H; NH-Arg) 7.34; m (0.2H; Cα-Pro) 4.73; m (0.8H; Cα-Pro) 4.61; m (0.2H; Cα-Pro) 4.39; m (0.8H; Cα-Pro) 4.33; m (7H; Cα-Arg and -Gly, and 2Cδ-Pro) 3.83÷3.26; m (2H; Cδ-Arg) 3.00; m (12H; Cβ- and Cγ-Pro and -Arg) 2.22÷1.26; s (3H; CH$_3$COO$^-$) 1.83.

EXAMPLE 12

H-(Et)Lys-Pro-OH.AcOH

The compound of example 4, B] (0.4 g, 0.82 mmoles) was dissolved at 0° C. in concentrated HCl (10 ml). After 8 min the solution was diluted with water and concentrated under vacuum. The residue was diluted with water, washed with diethyl ether and freeze-dried. The crude product was purified by ion exchange chromatography, proceeding as described in Example 1, I], thus yielding 0.244 g of the title product.

HPLC: column temperature 60° C.; gradient (II) R.t. 7.9 min; purity 99.1% FAB-MS: m/z=272 amu [M+H]$^+$; $^1$H-NMR (200 MHz; DMSO): m (1H; Cα-Pro) 4.17; m (1H; Cδ-Pro) 3.48; m (1H; Cα-Lys) 3.34; m (2H; Cε-Lys) 2.73; m (2H; Et-(CH$_2$)) 2.44; m (4H; Cβ and Cγ-Pro) 2.10÷1.68; s (3H; CH$_3$—COO$^-$) 1.87; m (6H; Cβ, Cδ and Cγ-Lys) 1.64÷1.27; t (3H; Et-(CH$_3$)) 0.98.

EXAMPLE 13

H-Gly-(Et)Lys-Pro-DArg-OH.2AcOH

A] The compound of Example 4, E] (0.250 g, 0.44 mmoles) was reacted with H-DArg-OH (0.115 g, 0.66 mmoles) following the procedure described in Example 7, C]. There was obtained 0.3 g of Z-Gly-(Et)Lys(Boc)-Pro-DArg-OH.

HPLC: gradient (I) R.t. 20.5 min; purity 82%.

B] The compound under A] was treated as described in Example 1, H], thus yielding 0.125 g of Z-Gly-(Et)Lys-Pro-DArg-OH.TFA.

HPLC: gradient (I) R.t. 12.9 min; purity 98.9%.

C] The compound under B] was treated as described in Example 1, I]. there was obtained 0.065 g of the title product.

HPLC: gradient (II) R.t. 14.8 min; purity 98.1%. FAB-MS: m/z=485 amu [M+H]$^+$; $^1$H-NMR (200 MHz, DMSO): d (1H; Nα-DArg) 7.54; m (0.8H; Cα-Pro) 5.21; m (0.2H; Cα-Pro) 4.43; m (1H; Cα-Lys) 440:428; m (1H; Cα-Arg) 3.84; m (1H; Cδ-Pro and CH$_2$—N) 3.70÷3.16; s (2H; Cα-Gly) 3.41; m (2H; Cδ-Arg) 3.0; m (2H; Cε-Lys) 2.75; m (4H; Cβ andγ-Pro) 2.12÷1.75; s (6H; CH$_3$COO$^-$) 1.79; m (10H; Cβ- and Cγ-Arg; Cβ andγ andδ-Lys) 1.70÷1.14; t (2.4H; C.H$_3$—CH$_2$) 0.98; t (0.6H; C.H$_3$—CH$_2$) 0.89.

EXAMPLE 14

H-Gly-(Et)Lys-Pro-Lys-OH.AcOH

A] The compound of example 4, E] (0.394 g, 0.7 mmoles) was dissolved in a DMF/methylene chloride mixture (2:4, v/v, 6 ml) and sequentially added with BOP (0.326 g, 0.735 mmoles), HOBT monohydrate (0.112 g, 0.735 mmoles), TEA (0.308 ml, 2.2 mmoles) and H-Lys(Boc)-OtBu.HCl (0.250 g, 0.735 mmoles).

After 90 min of stirring at room temperature, the mixture was evaporated under vacuum and the-residue was taken up in ethyl acetate (40 ml) and washed with 5% sodium hydrogencarbonate, 2.5% potassium hydrogen sulfate and water.

The organic phase was dried and evaporated under vacuum. There was obtained 0.53 g of Z-Gly-(Et)Lys(Boc)-Pro-Lys(Boc)-OtBu.

HPLC: gradient (I) R.t. 29.6 min; purity 90%.

B] Starting the compound under A] (0.34 g, 0.4 mmoles), and substantially proceeding as described in Example 1, H–I], there was obtained 0.1 g of the title product.

HPLC gradient (II) R.t. 7.75 min; purity 98.9%. FAB-MS: m/z=456 amu [M+H]$^+$; $^1$H-NMR (200 MHz; DMSO): d (1H; Nα-Lys$_4$) 7.08; m (1H; Cα-Pro) 5.21; m (1H; Cα-Lys$_2$) 4.26÷4.15; s (2N; Cα-Gly) 3.41; t (2H; Cε-Lys$_2$) 2.74; t (2H; Cε-Lys$_4$) 2.65; m (2H; CH$_3$-C.H$_2$) 2.51; m (4H; Cβ+γ-Pro) 2.12÷1.75; s (3H CH$_3$COO$^-$) 1.82; m (12H; Cβ+γ+δ-Lys$_2$) 1.70÷1.10; t (2.4H; C.H$_3$—Cu$_2$) 0.95; t (0.6H; C.H$_3$—Cu$_2$) 0.85.

EXAMPLE 15

H-Gly-(Et)Lys-Pro-Arg-OH.2AcOH

A] Z-Gly-OH (0.345 g, 1.65 mmoles) was dissolved in 30 ml of DMF/methylene chloride (4:6 v/v) and sequentially added with PyBrop (0.77 g, 1.65 mmoles), diisopropylethylamine (0.83 ml, 4.95 mmoles) and the solid obtained under example 2, B] (0.28 g, 0.33 mmoles) dissolved in 6 ml of the same mixture. The reaction mixture was left under stirring for 80 minutes. The solvent was then evaporated under vacuum and the residue taken up in ethyl acetate and washed with 5% sodium hydrocarbonate, 2.5% potassium hydrogen sulfate and water till neutrality. The organic phase was anhydrified and evaporated under vacuum. There was obtained 0.33 g of Z-Gly-(Et)Lys(Boc)-Pro-Arg(Pmc)-OtBu.

B] Starting from 0.3 g of the compound under A] and proceeding as described in Example 1, H], there was obtained 0.83 g of Z-Gly-(Et)Lys-Pro-Arg-OH.

HPLC: gradient (I) R.t. 12 min; purity 94%.

C] The compound under B] was purified by ion-exchange chromatography on a CM-Sephadex C-25 column (16×200 mm) by eluting at 3 ml/min with a gradient of ammonium acetate at pH=6 from 0.02M to 0.2 M in 270 minutes. The fractions collected were analyzed by HPLC and the ones containing the pure product were joined and freeze-dried more times yielding 0.067 g of Z-Gly-(Et)Lys-Pro-Arg-OH.2AcOH.

HPLC: gradient (I) R.t. 12 min; purity 97.5%. FAB-MS: m/z=619 amu [M+H]$^+$. $^1$H-NMR (200 MHz; DMSO): t (1H; NH-Gly) 7.46; m (5H; CH-aryl) 7.37; d (1H; NH-Lys) 7.24; m (1H; Cα-Lys) 5.19; s (2H; Cα-Arg) 5.05; m (1H; Cα-Pro) 4.23; m (2H; Cα-Gly) 3.92; m (1H; Cα-Arg) 3.81; m (2H; Cδ-Pro) 3.58; m (2H; CH$_2$-Et) 3.46; m (2H; Cδ-Arg) 2.99; m (2H; Cε-Lys) 2.65; m (4H; Cβ- and Cγ-Pro) 2.03÷1.76; m (19H; Cβ andγ-Lys and -Arg and Cδ-Lys) 1.69÷1.19; s (6H; CH$_3$COO$^-$) 1.66; t (3H; CH$_3$-Et) 1.04.

The compounds of the present invention showed to be endowed with cardiovascular and anti-inflammatory activity. In particular, they showed to be useful as therapeutic agents against septic shock and ischemia and/or ischemia and reperfusion states.

This activity was determined by means of the following pharmacological test.

Male Sprague Dawley rats (175–200 g, Charles river, Calco, Italy) were intravenously injected with a dose of LPS (Salmonella Enteritidis, Sigma) in 0.2 ml of physiological solution, previously determined on the same batch of animals, as giving about 30% survival. Thereafter they were randomized into groups of at least 18 animals and each immediately inoculated intravenously with 3 μg/kg of some of the compounds representative of the invention. One group of animals was treated with LPS only and considered as the control. The animals were monitored for the following 7 days to determine their survival.

The results are set forth in the following Table 1.

TABLE 1

| Example | Survival percentage |
| --- | --- |
| (control) | 23 |
| 3 | 71 |
| 4 | 43 |
| 5 | 52 |
| 7 | 67 |
| 9 | 39 |
| 10 | 43 |
| 11 | 57 |
| 12 | 44 |
| 14 | 48 |
| 15 | 33 |

The cardiovascular activity of the compounds of the invention was investigated by means of a test aiming at evaluating the cardioprotective activity following ischemia induced by the occlusion of the left coronary artery in the anestethized rat, performed substantially as described by C. Clark et al. Journ. Exp. Methods, 3, 357, 1980. It is known that the occlusion of the coronary artery causes several events altering the ECG-pattern including, among others, hypoxia, arrhythmias, with eventual death of the laboratory animals.

In this test, male Wistar rats, (350–450 g, Charles River) were divided into groups of at least 18 animals, anesthethized with nembutal (65 mg/kg i.p.) and each connected to an electrocardiograph for continuously monitoring the ECG. The animals, maintained under artificial ventilation, underwent thoracotomy and, after incision of the pericardium, a suture thread was passed around the left coronary artery, near to its origins. The animals were then administered intravenously with 0.1 μg/kg/min of the compounds of the invention dissolved in saline. One group of animals (control group) were administered intravenously with saline (5 ml/kg/hr). After 15 minutes recovery, and provided that electocardiographic alteration was not recorded, the left coronary artery was ligated and the ligature was maintained for 30 minutes. During this period the animals were monitored and ventricular tachycardia (VT), ventricular fibrillations (VF) and mortality were7 assessed.

The results are set fourth in the following table 2.

TABLE 2

| Example | Incidence % | | Mortality % |
| --- | --- | --- | --- |
| | V.T. | V.F. | |
| Control | 100 | 86 | 29 |
| 5 | 78 | 0 | 0 |
| 7 | 100 | 50 | 12 |
| 8 | 100 | 38 | 25 |
| 12 | 10 | 75 | 12 |
| 13 | 100 | 50 | 0 |

Object of the present invention is also the use of the new oligopeptides in the treatment of cardiovascular and inflammatory pathologies, referring to all the industrial aspects connected to said use which include the pharmaceutical compositions thereof. Examples of such pharmaceutical compositions are tablets, sugar coated and film coated tablets, syrups and phials, the latter being suitable both for the oral and the intramuscolar or endovenous administration. Such compositions contain the active principle alone or in combination with common pharmaceutically acceptable carriers and excipients.

The dosage of active principle may vary within wide ranges depending on the compound employed which may be administered one or more times a day according to the therapeutic needs.

What is claimed is:

1. Oligopeptides of formula (I)

$$A_1—A_2—A_3—A_4 \qquad (I)$$

wherein $A_1$ is an aminoacid residue selected from the group consisting of threonine, leucine, isoleucine, valine, sarcosine, alanine, glycine and ($C_{2-6}$)acyl-glycine, or is absent;

$A_2$ is proline or N-α-substituted basic aminoacid residue selected from the group consisting of lysine, arginine and ornithine, N-α-substituted by at least one ($C_{1-6}$) alkyl, benzyl or ($C_{2-6}$)acyl group;

$A_3$ is an aminoacid residue selected from the group consisting of proline, leucine, isoleucine and valine;

$A_4$ is an aminoacid residue selected from the group consisting of arginine, lysine, leucine and glutamine, optionally amidated or esterified at the C-terminal position, or is an agmatine residue, or is absent;

when $A_2$ is N-α-substituted lysine, both $A_1$ and $A_4$ may be absent; the side-chain groups of the above aminoacid residues and of the agmatine residue may be optionally substituted by one or more ($C_{1-6}$)-alkyl, benzyl or ($C_{2-6}$)acyl groups, and each of said aminoacid residues may be in D- or L-form, or in form of one of the possible diastereoisomers or enantiomers;

and their salts with pharmaceutically acceptable acids or bases.

2. Oligopeptides as defined in claim 1, wherein $A_1$ is an aminoacid residue selected from the group consisting of glycine, threonine, leucine, isoleucine, valine, sarcosine, alanine and ($C_{2-6}$)acyl-glycine, or is absent;

$A_2$ is lysine, arginine or ornithine N-α-substituted by a $(C_{1-6})$alkyl, benzyl or $(C_{2-6})$acyl group; $A_3$ is proline; $A_4$ is glutamine, leucine, arginine, optionally amidated or esterified at the C-terminal position, or an agmatine residue, or is absent;

the side-chain groups of said aminoacid residue and of the agmatine residue may optionally be substituted by one or more substituents selected from the group consisting of $(C_{1-6})$alkyl, benzyl and $(C_{2-6})$acyl; and each of said aminoacid residue may be in D or L form, or in form of one of the possible diastereoisomers or enantiomers;

and the pharmaceutically acceptable acid or base salts thereof.

3. An oligopeptide as defined in claim 1, wherein $A_1$ is absent, $A_2$ is N α-acetyl-lysine, $A_3$ is proline and $A_4$ is arginine;

and the pharmaceutically acceptable acid or base salts thereof.

4. An oligopeptide as defined in claim 1, wherein $A_1$ is glycine, $A_2$ is N α-ethyl-lysine, $A_3$ is proline and $A_4$ is absent;

and the pharmaceutically acceptable acid or base salts thereof.

5. A pharmaceutical composition having cardiovascular and anti-inflammatory activities comprising as the principal active ingredient an oligopeptide according to claim 1 in admixture with a pharmaceutically acceptable carrier.

6. A method of treating a patient suffering from a cardiovascular or inflammatory disease which comprises administering to said patient an effective amount of a composition according to claim 5.

* * * * *